United States Patent
Rösel et al.

(10) Patent No.: US 6,287,453 B1
(45) Date of Patent: Sep. 11, 2001

(54) METHOD FOR THE DIAGNOSIS OF A CONTINUOUS-ACTION LAMBDA PROBE

(75) Inventors: Gerd Rösel; Hong Zhang, both of Regensburg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/408,681

(22) Filed: Sep. 30, 1999

(30) Foreign Application Priority Data

Sep. 30, 1998 (DE) ............................................. 198 44 994

(51) Int. Cl.[7] .................................................... F02D 41/14
(52) U.S. Cl. .......................... 205/783; 204/401; 73/1.06; 73/23.32; 123/688
(58) Field of Search .................................... 204/401, 425; 73/1.06, 23.32; 205/783.5, 784, 784.5, 783; 123/688; 422/83, 98; 436/137

(56) References Cited

U.S. PATENT DOCUMENTS

| 5,020,499 | * | 6/1991 | Kojima et al. | 204/401 |
| 5,052,361 | * | 10/1991 | Ono et al. | 123/688 |
| 5,423,203 | * | 6/1995 | Namiki et al. | 123/688 |
| 5,970,967 | * | 10/1999 | Uchikawa | 123/688 |
| 6,032,659 | * | 3/2000 | Yamashita et al. | 123/688 |

FOREIGN PATENT DOCUMENTS

| 0 616 119 A1 | 9/1994 | (EP) . |
| 0 652 358 A2 | 5/1995 | (EP) . |

OTHER PUBLICATIONS

"Comparison of the response rate of exhaust gas sensors in motor vehicles for fast lambda measurement on the basis of selected metal oxide thin films", VDE Reports, No. 939, 1992, pp. 15–21.

"Automatic Control of Cylinder by Cylinder Air–Fuel Mixture Using a Proportional Exhaust Gas Sensor" (Bush et al.), SAE Paper No. 940149, pp. 57–71.

* cited by examiner

*Primary Examiner*—Robert J. Warden, Sr.
*Assistant Examiner*—Kaj K. Olsen
(74) *Attorney, Agent, or Firm*—Herbert L. Lerner; Laurence A. Greenberg; Werner H. Stemer

(57) ABSTRACT

Periodic forced stimulations are asserted on setpoint values for a lambda control and a system response of a lambda control loop is simulated by a model that includes a sensor delay time as the model parameter. Amplitude gains of the model and the system are compared with each other and adapted according to the result of the comparison of the model parameters. If the adaptation value lies above a threshold, a lambda probe is classified as defective.

7 Claims, 2 Drawing Sheets

METHOD FOR THE DIAGNOSIS OF A CONTINUOUS-ACTION LAMBDA PROBE

BACKGROUND OF THE INVENTION

FIELD OF THE INVENTION

The invention relates to a method for the diagnosis of a continuous-action lambda probe disposed upstream of a catalytic converter of an internal combustion engine.

For controlling the mixture in an internal combustion engine, it is known to provide in the exhaust flow upstream of the catalytic converter, serving for the conversion of harmful exhaust gas constituents, an oxygen sensor or probe, the output signal of which changes in dependence on an oxygen concentration in the exhaust gas.

In addition to so-called sudden-change probes, also referred to as binary probes, the output signal of which changes suddenly both when there is a transition from a rich mixture to a lean mixture and when there is a transition from a lean mixture to a rich mixture (sudden voltage change with the air-fuel coefficient $\lambda=1$), oxygen probes with a continuous characteristic curve are also used. These have a continuous, for example linear, dependence of the output signal on the air-fuel coefficient $\lambda$ and, in addition, a low rise time. (SAE Paper 940149 "Automatic Control of Cylinder Air-Fuel Mixture Using a Proportional Exhaust Gas Sensor").

Such an oxygen probe with a continuous output characteristic, referred to in the following simply as a continuous-action lambda probe, is constructed for example on the basis of strontium titanate ($SrTiO_3$) by thin-film technology (VDI Berichte 939, Düsseldorf 1992, "Vergleich der Ansprechgeschwindigkeit von KFZ Abgassensoren zur schnellen Lambdamessung auf der Grundlage von ausgewählten Metalloxiddünnfilmen" [Comparison Of The Rate Of Response Of Motor Vehicle Exhaust Sensors For Rapid Lambda Measurement On The Basis Of Selected Metal-Oxide Thin Films]).

The use of a continuous-action lambda probe results in the changeover from two-point lambda control to continuous lambda control. In order not to exceed the statutory exhaust-emission limit values, the failure of exhaust-relevant components must be detected and indicated (onboard diagnostics).

It is therefore necessary to check the functioning capability of the lambda probes as well. It is known from Published European Patent Application EP 0 616 119 A1 in the case of a lambda probe disposed upstream of the catalytic converter (pre-cat probe) to measure the switching times within which the output signal of the lambda probe switches over during its sudden-changing function from the high voltage value, which indicates a rich mixture (rich voltage), to a low voltage value, which indicates a lean mixture (lean voltage). The magnitude of these switching times is a measure of the functioning capability of the lambda probe disposed upstream of the catalytic converter.

A further method for checking the dynamic functioning capability of pre-cat lambda probes is described in Published European Patent EP 0 652 358 A2. There, the holding times within which the lambda probe signal indicates a rich or lean mixture are measured. The pre-cat lambda probe is then classified as operating correctly if both the rich and the lean holding times are less than prescribed limit values assigned to the individual holding times.

SUMMARY OF THE INVENTION

It is accordingly an object of the invention to provide a method for the diagnosis of a continuous-action lambda probe which overcomes the above-mentioned disadvantages of the prior art methods of this general type, in which the functioning capability of a lambda probe having an output signal with a continuous characteristic curve and disposed upstream of a catalytic converter in the exhaust flow of an internal combustion engine can be checked in a closed control loop.

With the foregoing and other objects in view there is provided, in accordance with the invention, a method for diagnosing a lambda probe disposed upstream of a catalytic converter of an internal combustion engine, the lambda probe outputting an output signal having a continuous characteristic curve received as an input variable of a lambda control loop, the method which includes:

superposing a periodic forced stimulation at a prescribed frequency and amplitude on a required value for an air-fuel ratio;

simulating a system response of the lambda control loop with a model having a sensor delay time as a model parameter;

determining amplitude gains of the model and the lambda control loop and performing a comparison of the amplitude gains with each other;

performing a modification of the model parameter, the sensor delay time, in accordance with a result of the comparison of the amplitude gains; and classifying the lambda probe as defective if a value of the modification of the model parameter exceeds a prescribed threshold value.

For the diagnosis of the lambda probe, forced stimulations are asserted on the closed lambda control loop. A forced stimulation brings about a periodic change in the value of the air-fuel ratio $\lambda$ by a stoichiometric ratio $\lambda=1$ and is described by applicable parameters, such as amplitude and frequency for example. To realize the prescribed situation as exactly as possible in the closed lambda control loop, a compensation of the dynamic response of the controlled system is required. This compensation of the system response can also be used to draw conclusions as to a change in the delay time of the lambda probe. The change in the dynamic response of the lambda probe is observed when there are aging effects or contamination of the probe. The compensation results can consequently be improved by an adaptation of the delay time of the lambda probe. The adaptation of the model parameters of the lambda probe allows the aging and contamination effects of the probe to be taken into account for the lambda control and for the compensation of the system response as well as the detection of a defective lambda probe, if applicable.

For the method described there has to be a continuous-action lambda probe upstream of the catalytic converter. The continuous-action lambda probe is the measuring element of the lambda control, which reduces deviations in the fuel-air ratio from a required value. The required value of the fuel-air ratio, the setpoint value of the control, is superposed with selectively periodic forced stimulations, which are prescribed for example with respect to amplitude and frequency (for example square-wave signal sequences) in such a way that the requirements of the internal combustion engine and the catalytic converter are taken into account in the best possible way. In order to realize in the best possible way the parameters, fixed by amplitude and frequency, of the forced stimulation in the closed control loop of the lambda control, a compensation of the dynamic response of the controlled system under lambda control is required. For an internal combustion engine, the system response can be characterized by the time lag between the load signal and the measured value acquisition of the lambda probe and the dynamic response of the lambda probe as a first-order time delay element. For the modeling of the time lag there are two fundamental possibilities. On the one hand, the time lag may be realized in the engine control by a shift register or the like, considerable expenditure being required for this to be realized on account of the great time lag at low engine speed and load. On the other hand, the time lag may be modeled by a finite-dimensional approximation, such as a Pad-approximation. In both cases, the parameters of the model of the time lag are adapted according to the operating point of the engine as functions of engine speed and load. Even when a low-order Pad-approximation (for example of the second order) is used, the compensation of the system response in the control loop has the effect that the forced stimulation characterized by amplitude and frequency can be realized in wide frequency ranges with minor errors.

It is also known that the dynamic response of the lambda probe changes due to aging and contaminating processes. On the one hand, these changes influence the controlling quality of the lambda control. On the other hand, such effects must be detected by a diagnosis process, so that a defective lambda probe is detected when there are excessive deviations in the probe response from a nominal response, which lead to the emission limit values being exceeded. According to the invention, conclusions concerning the described changes in the sensor response are drawn from a comparison between the system response and the model response of the system (nominal model) under forced stimulations. The system response is subject to drift (for example caused by the effects of contamination of the probe) and there are consequently deviations from the nominal model. An adaptation of the model parameter for the sensor response is made possible by the evaluation of an amplitude condition. For this purpose, it is necessary that the model of the time lag element is either a time lag element or a time lag approximation with a strict all-pass character (i.e. the degree of the numerator polynomial and the degree of the denominator polynomial of the transient function are equal). As a result, the linearized amplitude response of the system and system model are determined only by the sensor response. Deviations between the model and sensor response above the frequency fixed by the attenuation response of the sensor can be detected by a comparison of the amplitude gains of the system and model. That is to say that the fundamental harmonic of the forced stimulation must be so great that differences in the amplitude response of the model and the system can occur.

The small periodic changes in the fuel/air ratio brought about by the forced stimulation will also induce the conversion reactions in the catalytic converter, which leads to an improvement in the surge-loading capability of the catalytic converter.

Other features which are considered as characteristic for the invention are set forth in the appended claims.

Although the invention is illustrated and described herein as embodied in a method for the diagnosis of a continuous-action lambda probe, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
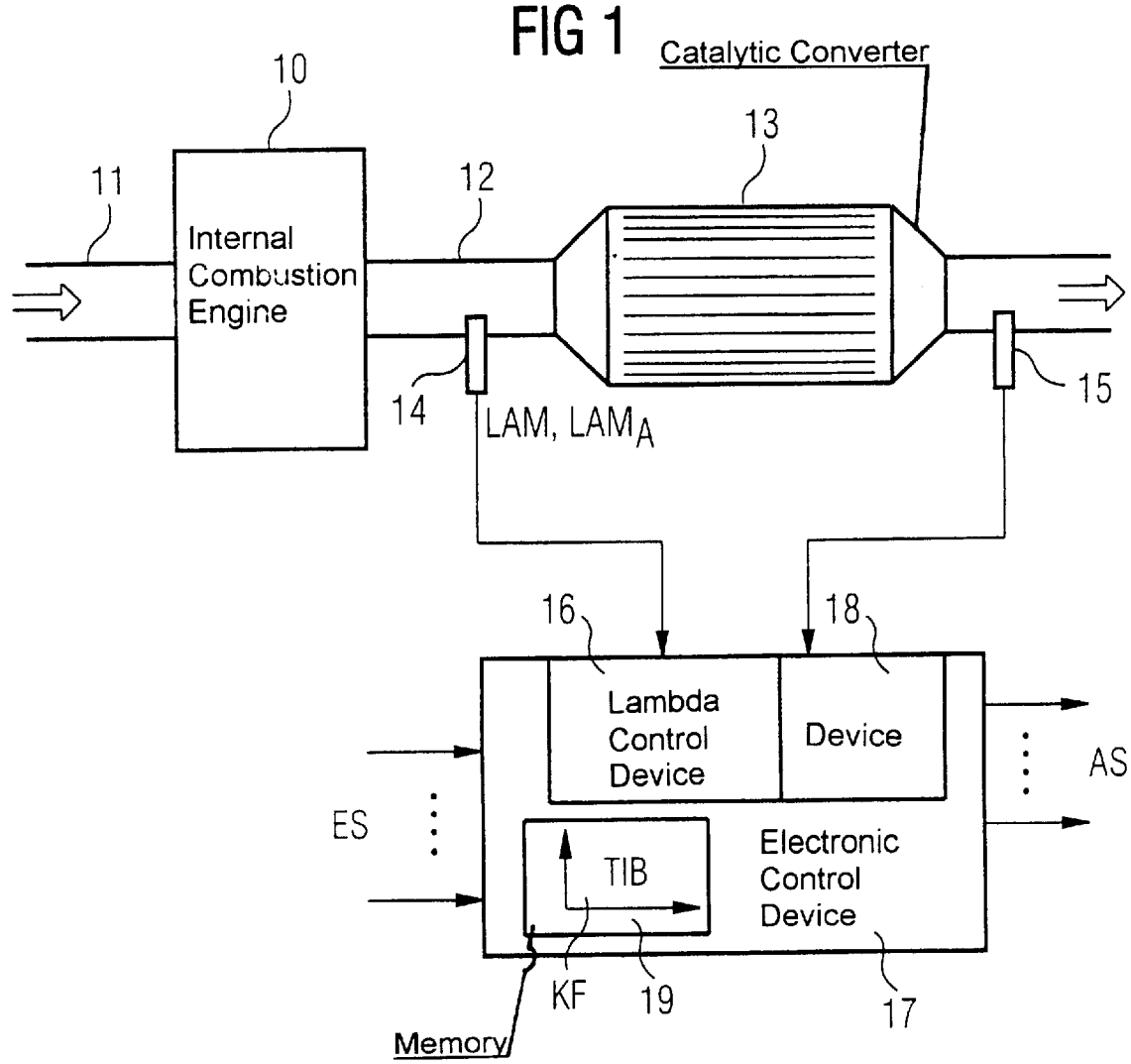
FIG. 1 is a diagrammatic, block diagram of an internal combustion engine with an associated exhaust system and an electrical control device.

In all the figures of the drawing, sub-features and integral parts that correspond to one another bear the same reference symbol in each case. Referring now to the figures of the drawing in detail and first, particularly, to FIG. 1 thereof, there is shown an internal combustion engine 10, which is connected to an intake tract 11 and an exhaust tract 12. Disposed in the exhaust tract 12 is a catalytic converter 13, for example a three-way catalytic converter, serving for the conversion of harmful exhaust gas constituents. A direction of the fed-in combustion air, and of the exhaust flow, is depicted by arrow symbols. Disposed upstream of the catalytic converter 13 is a first lambda probe 14, disposed downstream of the catalytic converter 13 is a second lambda probe 15. Used as the first lambda probe 14 is a probe of which the characteristic curve for the output signal in the range around $\lambda=1$ has a continuous, preferably linear, dependence on the lambda value and serves in a conventional way for mixture control. It emits an output signal LAM to a lambda control device 16, which is preferably integrated in an electronic control device 17 of the internal combustion engine 10. An amplitude of the output signal of the linear probe 14 is denoted by $LAM_A$. The lambda probe 15 disposed after the catalytic converter 13 serves for checking the catalyst efficiency and may likewise be a linear probe or a so-called sudden-change probe, the output signal of which changes suddenly when there is a transition from a rich mixture to a lean mixture and when there is a transition from a lean mixture to a rich mixture with the air-fuel coefficient $\lambda=1$. The output signal, not denoted any more precisely, of the lambda probe 15 is fed to a device 18 for checking the catalytic converter 13, which is connected with the lambda control device 16. By comparing and evaluating the signals supplied by the two probes 14, 15, the converting capability and consequently also the efficiency of the catalytic converter 13 can be concluded.

The lambda control device 16 also includes, inter alia, the functional blocks BL1, BL2, BL3, explained in more detail with reference to FIG. 2. The electronic control device 16 of the internal combustion engine 10 undertakes not only an ignition control but also many further functions in an open-loop and closed-loop control of the internal combustion engine 10, in particular the fuel injection. For this purpose, a basic injection time TIB, dependent on a load parameter (for example air mass flow or intake pipe pressure) and the engine speed is stored in a characteristic map KF in a memory 19 of the control device 17 and is further adapted, i.e. corrected, with the aid of known correction algorithms in certain operating states of the internal combustion engine 10. A correction factor is provided here by the lambda control device 16. The input and output signals for the control device 17 that are necessary for further operation of the internal combustion engine 10 are denoted generally in FIG. 1 by ES and AS, respectively.

Figure 2:
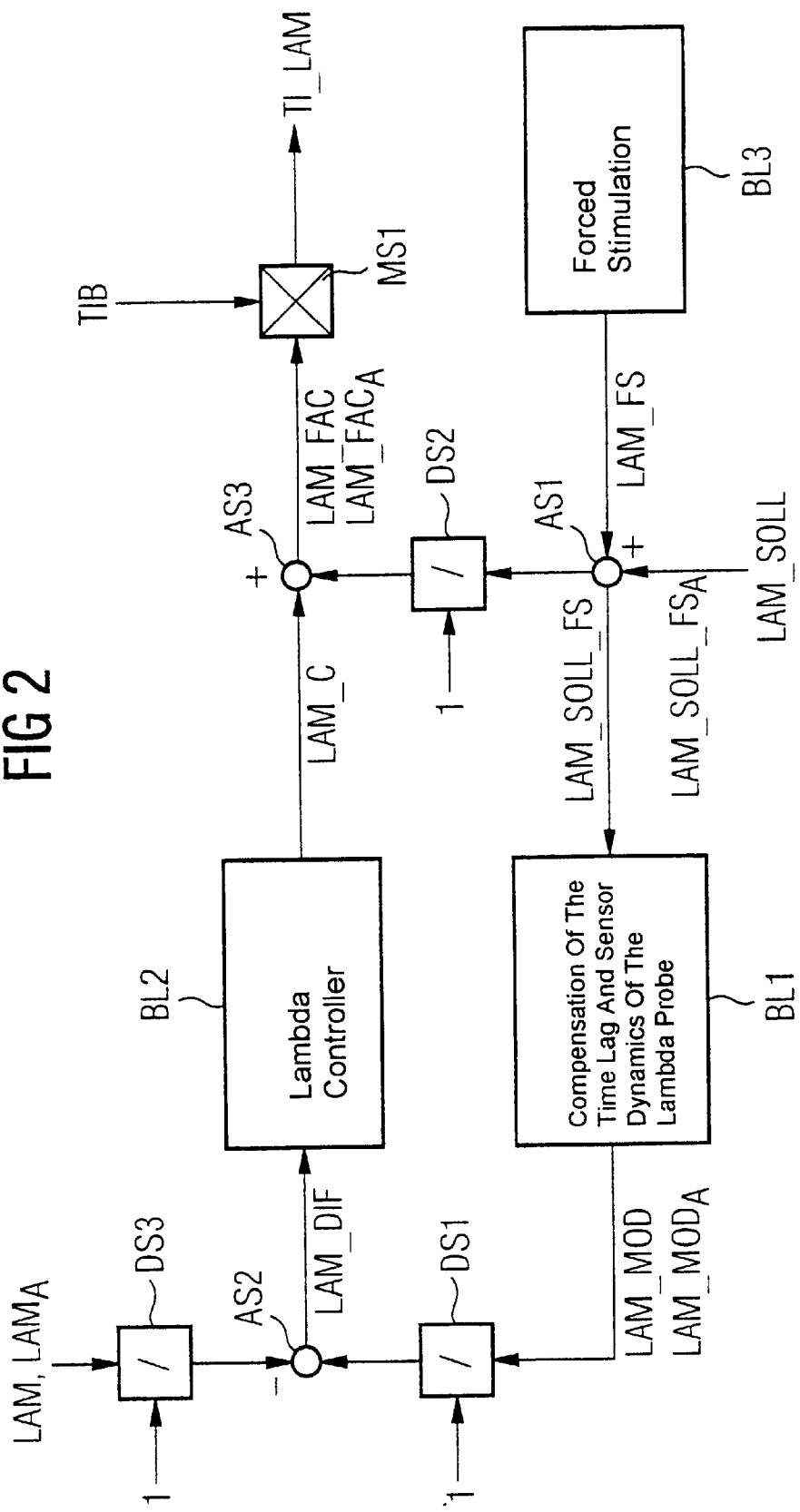
FIG. 2 is a block diagram of the structure of a lambda control having system response compensation circuitry.

In FIG. 2, LAM_SOLL denotes a prescribed lambda setpoint value, which may either be specifically prescribed as a constant factor, for example equal to 1 for a stoichiometric mixture, read out from a characteristic map according to the operating point of the internal combustion engine 10 or be calculated on the basis of operating parameters. The setpoint value LAM_SOLL is passed to an addition stage AS1.

The block BL3 contains a signal generator known per se, which generates a periodic oscillation at a specific frequency and amplitude. This may preferably be a square-wave oscillation, which is determined by its frequency and amplitude. In addition, however, a sawtooth oscillation, which is characterized by its amplitude, rise time and frequency, or any desired, periodic signal waveform (for example sinusoidal form) is also possible.

The output signal LAM_FS of the block BL3 (the abbreviation FS stands for forced stimulation) is superposed with the prescribed lambda setpoint value LAM_SOLL. For this purpose, it is likewise passed to the addition stage AS1. Such a forced stimulation has the effect of deliberately bringing about small periodic changes in the fuel/air ratio, i.e. the mixture to be fed to the internal combustion engine 10 is deliberately made periodically richer and leaner. A signal present at the output of the addition stage AS1 is denoted by LAM_SOLL_FS and the internal combustion engine 10 is to be operated with this value, taking the forced stimulation into account. To be able to realize the forced stimulations in the closed control loop of the lambda control with great accuracy, a model of the controlled system of the lambda control is required. The block BL1 represents this model and allows a compensation of the dynamic response of the controlled system. The compensation of the system response can also be used to draw conclusions as to a change in the delay time of the lambda probe.

The system response of the internal combustion engine 10 is characterized by the time lag between the injection operation and the measured value acquisition of the lambda probe and the dynamic response of the lambda probe itself. The delay response is represented by a first-order time lag element. Since the time lag element has an amplitude gain of 1 in the entire frequency range, only the sensor dynamics are significant. The model parameter for the block BL1 is therefore the sensor delay time for describing the probe response. The sensor delay time for a correctly operating, i.e. non-aged, lambda probe is applied. The value is determined on the test bench.

The output variable of the block BL1 is the model output signal LAM_MOD, which is passed to a division stage DS1. There, the inverse value of the model output signal LAM_MOD is formed. By this division, a linear control loop response is obtained at the operating point, otherwise the response is unsymmetrical, dependent on whether deviations occur in the direction of a rich mixture or lean mixture. The inverse value of the model output variable 1/LAM_MOD is passed to an addition point AS2. The lambda probe 14 supplies the lambda value LAM according to the residual oxygen content in the exhaust gas. From the measured value the inverse value is likewise formed (division stage DS3) and then passed to the addition point AS2, where it is subtracted from the inverse value of the model output signal. A system deviation LAM_DIF consequently formed is an input variable for the block BL2, which represents a continuous-action lambda controller known per se. It may be realized for example as a PID controller (proportional-integral-differential controller).

An output signal of the block BL2 represents a manipulated variable LAM_C of the control loop, which is passed to an addition stage AS3. A further input variable of the addition stage AS3 is the inverse value (formed in the division stage DS2) of the input signal of the system model LAM_SOLL_FS. The sum of the two values gives a dimensionless factor LAM_FAC, by which the basic injection time TIB, read out from a characteristic map of load and speed and expressed for example in msec, is multiplied in a multiplication stage MS1. An injection time TI_LAM that takes the influence of the lambda control into account is obtained as the result of this.

Further correction factors that influence the basic injection time TIB are not represented here.

In the following it is explained how on the basis of the structure specified, the lambda probe can be diagnosed with regard to its dynamics.

Aging and/or contamination effects cause the sensor delay time to change, i.e. the lambda probe becomes slower. Consequently, the amplitude gain above a cut-off frequency, which is dependent on the probe aging, also changes. By evaluating the relationship between the amplitude gain of the model and that of the actual system, an adaptation of the model parameter, sensor delay time, can take place. If in the course of this adaptation a prescribed threshold value is exceeded, the lambda probe no longer meets the requirements with regard to its dynamic properties and is classified as defective.

The amplitude gains of the model LAM_MOD$_A$/LAM_SOLL_FS$_A$ and the system LAM$_A$/LAM_FAC$_A$ are determined and the two values are compared with each other.

If the relationship:

$$\text{LAM\_MOD}_A/\text{LAM\_SOLL\_FS}_A > \text{LAM}_A/\text{LAM\_FAC}_A$$

applies, the sensor delay time is greater than the corresponding model parameter and the originally applied model delay time is adapted, in this case it is increased.

Where:
LAM_MOD is the amplitude of the output signal of the system model (block BL1)
LAM_SOLL_FS$_A$ is the amplitude of the input signal of the system model (block BL1)
LAM$_A$ is the amplitude of the measuring signal of the lambda probe
LAM_FAC$_A$ is the amplitude of the input signal of the controlled system.

The four variables indicated are free from direct components.

Otherwise, if the relationship:

$$\text{LAM\_MOD}_A/\text{LAM\_SOLL\_FS}_A < \text{LAM}_A/\text{LAM\_FAC}_A$$

applies, the sensor delay time is less than the corresponding parameter of the model and the originally applied model delay time is likewise adapted, but in this case it is reduced.

The individual amplitude gains are determined, in that the amplitudes of the model and system variables, i.e. the maximum values within a period duration, are respectively determined. The amplitude of the signal of the forced stimulation is asserted and is consequently also known.

A prerequisite for such a method of diagnosis is that the chosen frequency of the forced stimulation lies above a frequency fixed by the sensor response from which an attenuation occurs (break frequency in the amplitude response of the sensor). On the basis of such a comparison between the model response and system response, an adaptation of the model parameter for describing the sensor response can take place. If the value of the adaptation of the model parameter exceeds a defined, speed-dependent and load-dependent threshold value, so that the emissions exceed a limit value, the lambda probe is classified as defective.

With the aid of the forced stimulation described, a diagnosis of the efficiency of the catalytic converter 13 can also take place by evaluating the signal of the continuous-action lambda probe 14 upstream of the catalytic converter 13 and the signal of the two-point lambda probe 15 downstream of the catalytic converter 15. In principle, similar diagnostic algorithms as in the case of conventional lambda controls with a binary lambda probe are possible in this case. The forced stimulation is required when a continuous-action lambda control is used, since in the case of this control principle there do not occur any limit cycles of the kind which can be observed in the case of two-point control and can be evaluated for diagnosis of the catalytic converter.

We claim:

1. A method for diagnosing a lambda probe disposed upstream of a catalytic converter of an internal combustion engine producing an air fuel coefficient (λ), the lambda probe having an amplitude gain and outputting an output signal having a continuous characteristic curve with respect to the air fuel coefficient (λ) received as an input variable of a lambda control loop, the method which comprises:

superposing a periodic forced stimulation at a prescribed frequency and amplitude on a required value for an air-fuel ratio;

simulating a system response of the lambda control loop to said superposing step with a model having a sensor delay time as a model parameter, the model having an amplitude gain;

determining the amplitude gains of the model and the lambda control loop and performing a comparison of the amplitude gains with each other;

performing a modification of the model parameter, the sensor delay time, in accordance with a result of the comparison of the amplitude gains; and classifying the lambda probe as defective if a value of the modification of the model parameter exceeds a prescribed threshold value.

2. The method according to claim 1, which comprises increasing the sensor delay time if the following applies in regards to the amplitude gains:

$$LAM\_MOD_A/LAM\_SOLL\_FS_A > LAM_A/LAM\_FAC_A,$$

where:

$LAM\_MOD_A$—is an amplitude of an output signal of the model, $LAM\_SOLL\_FS_A$—is an amplitude of an input signal of the model, $LAM_A$—is an amplitude of the output signal of the lambda probe, and $LAM\_FAC_A$—is an amplitude of an input signal of a controlled system.

3. The method according to claim 1, which comprises reducing the sensor delay time if the following applies in regards to the amplitude gains:

$$LAM\_MOD_A/LAM\_SOLL\_FSA < LAMA/LAM\_FACA$$

where:

LAM_MOD—is an amplitude of an output signal of the model,

LAM_SOLL_FSA—is an amplitude of an input signal of the model,

LAMA—is an amplitude of the output signal of the lambda probe, and

LAM_FACA—is an amplitude of an input signal of a controlled system.

4. The method according to claim 1, which comprises fixing the prescribed threshold value according to a speed and a load of the internal combustion engine.

5. The method according to claim 1, which comprises using a square-wave oscillation as the periodic forced stimulation.

6. The method according to claim 1, which comprises using a sinusoidal oscillation as the periodic forced stimulation.

7. The method according to claim 1, which comprises using a sawtooth-shaped oscillation characterized by its amplitude, rise time and frequency as the periodic forced stimulation.

* * * * *